US00PP18935P2

(12) United States Plant Patent

Serimian et al.

(10) Patent No.: US PP18,935 P2

(45) Date of Patent: Jun. 17, 2008

(54) NECTARINE TREE DENOMINATED 'SUMMER LION IV'

(50) Latin Name: ***Prunus persica* var. *nectarine***
Varietal Denomination: Summer Lion IV

(76) Inventors: Donald M. Serimian, 10463 S. Del Rey Ave., Selma, CA (US) 93662; Lionel M. Serimian, 10463 S. Del Rey Ave., Selma, CA (US) 93662

( * ) Notice: Subject to any disclaimer, the term of this patent is extended or adjusted under 35 U.S.C. 154(b) by 7 days.

(21) Appl. No.: 11/592,417

(22) Filed: Nov. 3, 2006

(51) Int. Cl.
*A01H 5/00* (2006.01)

(52) U.S. Cl. ..... Plt./192

(58) Field of Classification Search ..... Plt./190, Plt./192
See application file for complete search history.

(56) References Cited

U.S. PATENT DOCUMENTS

PP6,544 P * 1/1989 Serimian et al. ..... Plt./192

* cited by examiner

*Primary Examiner*—Wendy C. Haas
(74) *Attorney, Agent, or Firm*—Worrel & Worrel

(57) ABSTRACT

A new and distinct variety of nectarine tree which is somewhat similar to the 'Summer Lion II' nectarine tree but from which it is distinguished by producing fruit which are mature for harvesting and shipment approximately seven (7) days after 'Summer Lion II' fruit in the San Joaquin Valley of central California and wherein the fruit is of high quality and good flavor with dark red coloration over most of the fruit surface.

1 Drawing Sheet

Latin name of the genus and species of the plant claimed: *Prunus persica* var. nectarine.

BACKGROUND OF THE NEW VARIETY

The present invention relates to a new and distinct variety of nectarine tree, *Prunus persica* var *nectarina,* which will hereinafter be denominated varietally as the 'Summer Lion IV' nectarine tree, and, more particularly, to a nectarine tree which produces fruit which is mature for commercial harvesting and shipment approximately July 15$^{th}$ through July 30$^{th}$, or about one week after 'Summer Lion II' nectarine tree (U.S. Plant Pat. No. 6,544), in the San Joaquin Valley of central California. The subject new variety hereof has, in summary, fruit which is large in size with a moderately red and dark red blush color and a yellow-orange flesh color.

The discovery and development of new plant varieties is a daunting task. Nonetheless, these efforts take place in many areas of the world. The motivation for such efforts is both to assist mankind in the improvement of the varieties in a multitude of respects, as well as to achieve rewarding commercialization thereof. These activities have been particularly focused in the San Joaquin Valley of central California where growing conditions are quite favorable. As a consequence of these and other factors, a multitude of individuals, business entities, research institutions, universities and others have engaged in such research and development. The process is difficult, time consuming and expensive. As a consequence, these efforts are directed to the recovery of costs and, more typically, significant financial reward through commercialization. However, it is very difficult to select varieties which may achieve commercial success.

The new variety of nectarine tree of the present invention is believed by the inventors to be a promising candidate in a number of significant respects, as will hereinafter be set forth in greater detail.

ORIGIN AND ASEXUAL REPRODUCTION OF THE NEW VARIETY

The present variety of nectarine tree hereof was discovered by the inventors in their orchard located near Selma in the San Joaquin Valley of central California. The inventors discovered the variety as a newly found seedling in the spring of 2001, the result of cross pollination between the 'June Lion' nectarine tree (U.S. Plant Pat. No. 13,792) and 'Summer Lion II' nectarine tree (U.S. Plant Pat. No. 6,544). In the spring of 2001 the new variety of nectarine tree had budwood selected from the subject nectarine tree which was then grafted on Nemaguard rootstock planted in their test block in a 'Summer Lion II' nectarine orchard. The inventors have observed the asexually reproduced growth and fruit of the new variety and have found that, in all respects, the resulting progeny are identical to that of the original tree of the new variety.

SUMMARY OF THE NEW VARIETY

The nectarine tree of the new variety is characterized by producing a fruit which is ripe for commercial harvesting and shipment approximately July 15$^{th}$ through July 30$^{th}$ in the San Joaquin Valley of central California. This is about seven (7) days later than 'Summer Lion II' nectarine tree (U.S. Plant Pat. No. 6,544). The new variety of the present invention is distinguished from its parent trees primarily in the date of ripening, by being more intensely colored and by having slightly smaller fruit. The new variety of the present invention is most closely similar to the 'Summer Lion II' nectarine tree (U.S. Plant Pat. No. 6,544), but is distinguished therefrom in the aforementioned respects.

BRIEF DESCRIPTION OF THE DRAWING

The drawing is a color photograph displaying representative portions of the new variety of nectarine tree hereof with the fruit shown on the upper left first in a bottom plan view of the apex end thereof, a second shown in a top plan view exposing the base thereof, a third in a side elevation and a forth in the central right of the photograph sectioned and laid open to display in one section, the stone in place in its natural position in the pit well and the flesh thereof and, in the other section, the pit well with the stone thereof removed and the flesh of the fruit; a representative stone; and above and below representative foliage, all of the new variety of nectarine tree of the present invention.

DETAILED DESCRIPTION

Referring more specifically to the botanical details of the new variety of nectarine tree, the following has been observed under the ecological conditions prevailing at the orchard of origin in an experimental block near Selma, Calif. in the San Joaquin Valley of central California, in the United States of America. All major color code designations are by reference to the *Dictionary of Color,* by Maerz and Paul, First Edition, 1930. Common color names are also occasionally employed.

TREE

Generally:

*Size.*—Approximately 365.76 cm (12 feet) to 426.72 cm (14 feet) high with a spreading width of the branches of 304.8 cm (10 feet) to 396.24 cm (13 feet).

*Vigor.*—Very good with new growth of 91.44 cm (3 feet) in length.

*Chilling requirements.*—Normal for nectarine trees in the San Joaquin Valley of central California.

*Figure.*—Upright and spreading.

*Productivity.*—Very good to excellent for $5^{th}$ leaf.

*Regularity of bearing.*—Regular.

Trunk:

*Size.*—58.42 cm (23 inches) in circumference at 30.48 cm (12 inches) above the ground.

*Surface texture.*—Rough.

*Color.*—Pl.8 49 Rembrandt.

*Lenticels.*—Shape — Lenticular. Numbers — Abundant on trunk surface. Size — Length — Approximately 0.31 cm (0.12 inch). Width — Approximately 0.1 cm (0.04 inch).

Branches:

*Size.*—25.4 cm (10 inches), 33.02 cm (13 inches) above branch, angle of scaffold branches approximately 60°.

*Surface texture.*—Mature — Moderately smooth. Immature — Smooth.

*Color.*—Mature branches — Pl.8 J8 Java Brown to Pl.8 J11 Montella Tuscany. Immature branches — Pl.18 L8 Eve gr.

*Lenticels.*—Number — Many. Size — Approximately 0.31 cm (0.12 inch) long.

Leaves:

*Size.*—Length — 13.69 cm (5.39 inches) to 17.09 cm (6.73 inches). Width — 3.99 cm (1.57 inches) to 4.7 cm (1.85 inches).

*Shape.*—Lanceolate.

*Color.*—Upwardly Disposed Surface — Pl.22 L10 Brunswick Green. Downwardly Disposed Surface — Pl.20 K6 Piquant gr.

*Marginal form.*—Crenate.

*Leaf mid vein.*—Thickness — 0.1 cm (0.04 inch) to 2.01 cm (0.79 inch). Color — Pl.17 K5 Pale green.

*Leaf margin.*—Slightly undulate.

*Glandular characteristics.*—Shape — Reniform — from 1-3 at base or leaves alternate, usually two. Size — 0.1 cm (0.04 inch) to 0.15 cm (0.06 inch). Position — At or near base of leaf. Pattern — Alternate. Color — Pl.8 L7 Carbuncle.

*Petiole.*—Length — 0.81 cm (0.32 inch) to 0.99 cm (0.39 inch). Thickness — 0.2 cm (0.079 inch). Color — Pl.19 G6 Pistachio gr.

*Stipules.*—On younger growing tips — Shape — Linear. Size — Approximately 0.41 cm (0.16 inches). Color — Pl.19 A67 Seacrest becoming darker Pl.7 J8 Domingo and doubling with age.

Flowers:

*Flower buds.*—Pubescent. Shape — Conic. Size — Length — 0.71 cm (0.28 inch) to 0.79 cm (0.31 inch). Width — 0.71 cm (0.28 inch).

*Calyx.*—5 sepals with pubescent surface — veined. Color — Pl.55 L12 Vineyard Oporto+.

*Flowers.*—Date of bloom — Mar. 3, 2006, 50 to 75%. Size — Large when fully opened. Diameter — 3.4 cm (1.34 inch) to 4.32 cm (1.7 inch).

*Bloom quantity.*—Essentially on new growth — moderate, one to two blooms in cluster.

*Petals.*—Number — 5. Size — Generally large. Length — 1.7 cm (0.67 inch) to 2.01 cm (0.79 inch). Width — 1.6 cm (0.63 inch) to 1.83 cm (0.72 inch). Form — Broadly ovate with undulated margin. Color — Pl.1 D1 light pink to Pl.2 I1 light pink to Pl.1 I1 at base of petal at maturity.

*Claws.*—Short and truncate.

*Pedicel.*—Size — Length — short — 0.1 cm (0.04 inch). Width — 0.2 cm (0.079 inch).

*Sepals.*—Number — 5. Color — Pl.55 L8 Rubient. Size — Length — 0.79 cm (0.31 inch). Width — 0.61 cm (0.24 inch).

*Stamens.*—Number — Numerous, 28 to 34. Size — Length — 0.99 cm (0.39 inch) to 1.4 cm (0.55 inch).

*Filament.*—Color — Pl.1 C1 to Pl.1 I1.

*Anthers.*—Shape — Somewhat rounded. Color — Pl.7 H11 Casserole Brown, Gingerspice — Eskimo+.

*Pistil.*—Size — From 0.51 cm (0.2 inch) to 1.19 cm (0.47 inch). Color — Pale yellow-green.

*Ovary.*—Color — Pl.17 G8 Arcadian gr.

FRUIT

Maturity when described: Ripe for commercial harvesting and shipment approximately July $15^{th}$ through $30^{th}$ in the San Joaquin Valley of central California.

*Size.*—Large. Diameters in the Axial Plane — From 6.81 cm (2.68 inch) to 7.8 cm (3.07 inch). Transverse in the Suture Plane — 7.21 cm (2.84 inch) to 8.26 cm (3.25 inch). Transverse at Right Angles to Suture Plane — 6.5 cm (2.56 inch) to 7.01 cm (2.76 inch).

*Form.*—Uniformity — Good. Symmetrical or asymmetrical — Symmetrical. Suture — From apex to base — Visible and moderate. Ventral Surface — Smooth.

*Stem cavity.*—Shape — ovate. Size — Width — 0.99 cm (0.39 inch) to 1.5 cm (0.59 inch). Depth — 1.09 cm (0.43 inch) to 1.3 cm (0.51 inch). Length — 2 cm (0.79 inch) to 2.31 cm (0.91 inch).

*Stem.*—Size — Short — 0.61 cm (0.24 inch) to 1.09 cm (0.43 inch). Caliper — 0.46 cm (0.18 inch) to 0.56 cm (0.22 inch).

*Apex.*—Rounded.

*Pistil point.*—Oblique.

Skin/flesh:

*Thickness.*—Normal for nectarines.

*Texture.*—Firm, glabrous.

*Tendency to crack.*—None observed.

*Color.*—Blush Color — From Pl.5 L11 Brickdust to Pl.55 J12 Dahlia pr. Ground Color — Pl.9 K5 Apricot Y. Flesh Color — Pl.9 J5 Jonquil throughout from skin to the pit cavity with red flecking Pl.4 L10 Hollyberry. Color of Surface Pit Cavity — Pl.4 L10 Hollyberry with a number of red fibers on the pit cavity well. Color of Pit Well — Pl.4 L10 Hollyberry.

*Juice production.*—Moderate.

*Flavor.*—Very good.

*Aroma.*—Very aromatic.

*Texture.*—Firm.

*Fibers.*—Numbers — Few.

*Ripening.*—Evenly.

*Eating quality.*—Very good.

Stone:

*Free or cling.*—Freestone.

*Fibers.*—Numbers — Few. Length — 0.99 cm (0.39 inch) to 1.5 cm (0.59 inch).

*Size.*—Length — 3.61 cm (1.42 inch) to 4.19 cm (1.65 inch). Width — 3 cm (1.18 inch) to 3.2 cm (1.26 inch). Thickness — 2.11 cm (0.83 inch) to 2.49 cm (0.98 inch).

*Form.*—From ovate to obovate.

*Apex shape.*—Acute with a sharp tip.

*Color.*—Dry — Pl.55 J12 Dahlia Pr.

*Base shape.*—Flat with slanted sides.

*Hilum.*—Ovate with heavy collar. Length — 0.61 cm (0.24 inch) to 0.79 cm (0.31 inch).

*Ridges.*—Apical End — More heavily apparent. Dorsal Edge — Tightly grooved. Ventral Edge — Wider.

*Tendency to split.*—None observed.

Use: Fresh market.

Keeping and shipping quality: Very good.

Resistance to disease: None known.

Harvesting and shipping: July 15$^{th}$ through July 30$^{th}$.

Has the new variety been sold: No.

Has the new variety been publicly used or exhibited: No.

Have any reproducible parts of the plant been given away: No.

Although the new and distinct variety of nectarine tree possesses the described characteristics noted above as a result of the growing conditions prevailing near Selma in the central San Joaquin Valley of California, it is to be understood that variations of the usual magnitude and characteristics incident to changes in growing conditions, irrigation, fertilization, pruning, pest control, climatic variations and the like are to be expected.

Having thus described and illustrated our new variety of nectarine tree, what we claim as new and desire to be secured by Plant Letters Patent is:

1. A new and distinct variety of nectarine tree substantially as illustrated and described which is somewhat remotely similar to the 'Summer Lion II' nectarine tree (U.S. Plant Pat. No. 6,544), but from which it is distinguished by producing fruit which are mature for commercial harvesting and shipment approximately July 15$^{th}$ through July 30$^{th}$, or about seven days after the 'Summer Lion II' nectarine tree (U.S. Plant Pat. No. 6,544), in the San Joaquin Valley of central California and which has a distinct red coloration over its skin surface.

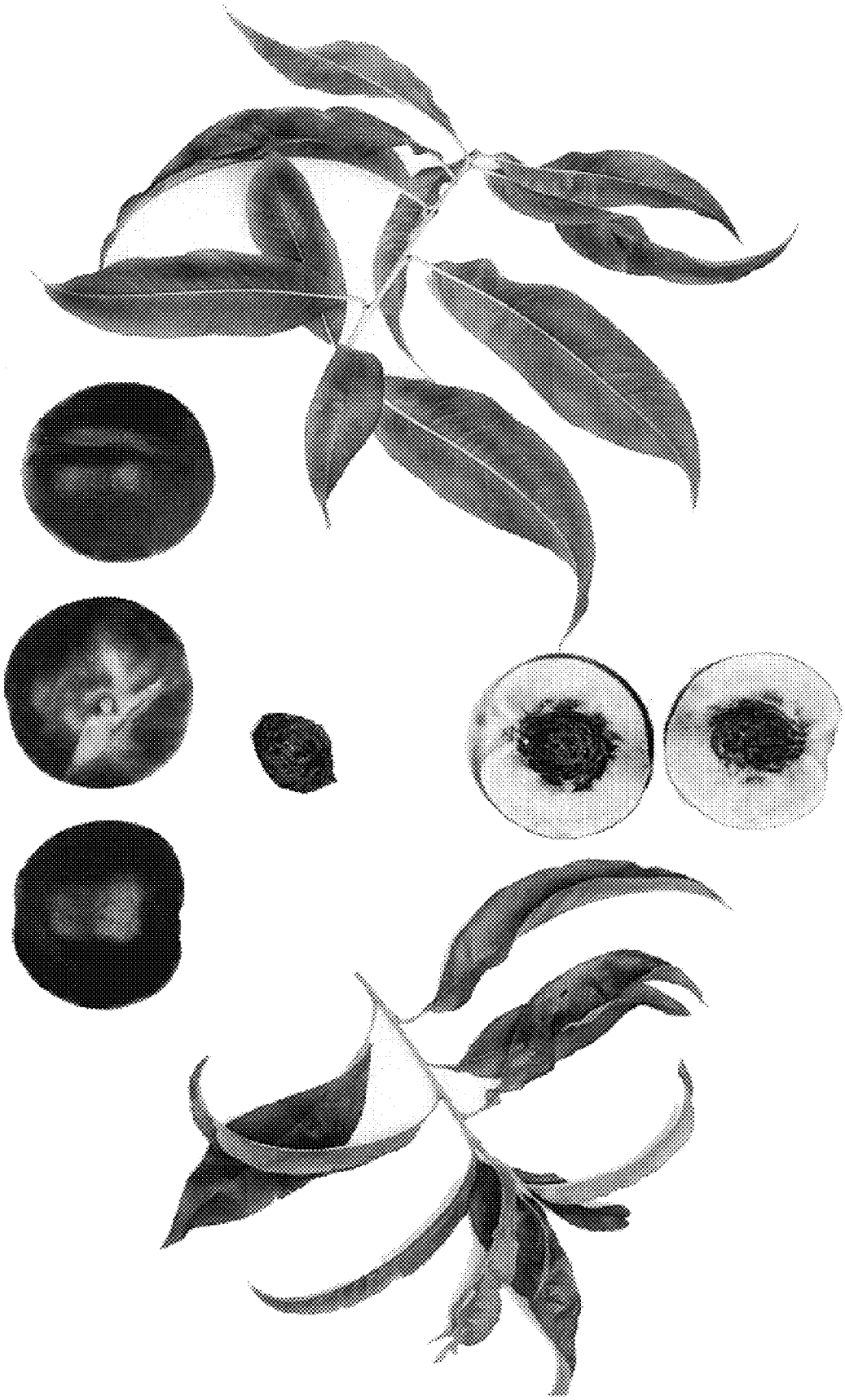

* * * * *